(12) United States Patent
Frey et al.

(10) Patent No.: US 8,580,195 B2
(45) Date of Patent: Nov. 12, 2013

(54) LABORATORY SYSTEM FOR HANDLING SAMPLE TUBE RACKS, AN ALIGNMENT ELEMENT FOR SAMPLE TUBE RACKS AND A RACK TRAY RECEIVER ASSEMBLY

(75) Inventors: Rolf Frey, Ebikon (CH); Fritz Goedl, Holzhausern (CH); Bruno Koch, Steinhausen (CH); Joachim Lackner, Mettmenstetten (CH); Ueli Stettler, Cham (CH); Lydia Stettler, legal representative, Cham (CH); Beat Widmer, Steinhausen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 609 days.

(21) Appl. No.: 12/460,822

(22) Filed: Jul. 23, 2009

(65) Prior Publication Data

US 2010/0028203 A1    Feb. 4, 2010

(30) Foreign Application Priority Data

Jul. 25, 2008 (EP) .................................... 08013459

(51) Int. Cl.
*G01N 21/00* (2006.01)
*G01N 31/00* (2006.01)
*G01N 33/00* (2006.01)
*G01N 35/02* (2006.01)

(52) U.S. Cl.
USPC .................... 422/63; 422/65; 436/47; 436/48

(58) Field of Classification Search
USPC ........ 422/63, 64, 65, 72, 500; 436/43, 45, 47, 436/48, 174, 180
See application file for complete search history.

(56) References Cited

U.S. PATENT DOCUMENTS

| | | | |
|---|---|---|---|
| 4,653,793 A | 3/1987 | Guinot et al. ................ | 294/86.4 |
| 5,242,659 A | 9/1993 | Wurschum ...................... | 422/65 |

(Continued)

FOREIGN PATENT DOCUMENTS

| | | | |
|---|---|---|---|
| DE | 3150672 | 7/1983 | ............... B23Q 3/10 |
| DE | 229370 | 11/1985 | ............. B65D 19/44 |

(Continued)

OTHER PUBLICATIONS

Handbook of Clinical Automation, Robotics and Optimization, G. Kost ed., Chapters 12 and 13, Wiley & Sons, Inc. (1996).

(Continued)

*Primary Examiner* — Jill Warden
*Assistant Examiner* — Charles D Hammond
(74) *Attorney, Agent, or Firm* — McDonnell Boehnen Hulbert & Berghoff LLP (57) ABSTRACT

A laboratory system for handling sample tube racks, an alignment element for sample tube racks and a rack tray receiver assembly are disclosed. The laboratory system to handle laboratory sample tube racks comprises a robotic arm (220) with a gripper (222) for gripping primary racks (PR), wherein the primary racks (PR) to be handled comprise a first end surface (76) and a second end surface (78), the first end surface (76) having a first surface geometry and the second end surface (78) having a second surface geometry, and wherein the gripper (222) comprises a first gripping arm (226) and a second gripping arm (228), with the first gripping arm (226) having a gripping surface being complementary to the first surface geometry, and the second gripping arm (228) having a gripping surface being complementary to the second surface geometry.

10 Claims, 9 Drawing Sheets

(56) References Cited

U.S. PATENT DOCUMENTS

| | | | |
|---|---|---|---|
| 5,417,922 A * | 5/1995 | Markin et al. | 422/65 |
| 5,620,894 A | 4/1997 | Barger et al. | 435/286.2 |
| 5,721,384 A | 2/1998 | Tanihata | 73/864.81 |
| 5,985,215 A | 11/1999 | Sakazume et al. | 422/67 |
| 6,068,437 A | 5/2000 | Boje et al. | 414/331.02 |
| 6,074,617 A * | 6/2000 | DeYoung et al. | 422/565 |
| 6,081,326 A | 6/2000 | Rousseau et al. | 356/246 |
| 6,220,451 B1 | 4/2001 | Hoffmann | 209/522 |
| 6,489,169 B1 * | 12/2002 | Cohen et al. | 436/47 |
| 6,586,255 B1 * | 7/2003 | Hubert et al. | 436/45 |
| 6,599,476 B1 | 7/2003 | Watson et al. | 422/63 |
| 6,926,058 B2 | 8/2005 | Sato et al. | 156/556 |
| 7,364,907 B2 | 4/2008 | Weselak et al. | 436/43 |
| 2002/0000730 A1 | 1/2002 | Murakami et al. | 294/1.1 |
| 2002/0023444 A1 | 2/2002 | Felder et al. | 62/177 |
| 2004/0213651 A1 | 10/2004 | Malin | 414/331.05 |
| 2005/0053454 A1 | 3/2005 | Wiggli et al. | 414/752.1 |
| 2006/0093529 A1 * | 5/2006 | Meyer et al. | 422/104 |
| 2006/0116269 A1 | 6/2006 | Lagarde | |
| 2006/0216199 A1 * | 9/2006 | Koike | 422/65 |
| 2006/0263270 A1 | 11/2006 | Rizzotte et al. | 422/104 |
| 2006/0266969 A1 | 11/2006 | Kawahara et al. | 251/149.6 |
| 2007/0014469 A1 | 1/2007 | Paillet et al. | 382/159 |
| 2007/0172396 A1 | 7/2007 | Neeper et al. | 422/104 |
| 2007/0207056 A1 * | 9/2007 | Veiner et al. | 422/63 |
| 2008/0063562 A1 | 3/2008 | Hoover et al. | 422/63 |
| 2008/0170967 A1 * | 7/2008 | Itoh | 422/104 |

FOREIGN PATENT DOCUMENTS

| | | | |
|---|---|---|---|
| DE | 19912211 | 12/2001 | G01N 35/04 |
| EP | 0 467 302 | 1/1992 | |
| EP | 1348965 | 10/2003 | G01N 35/04 |
| EP | 1353183 | 10/2003 | G01N 35/10 |
| EP | 1391402 | 2/2004 | B65G 1/04 |
| EP | 1541067 | 6/2005 | A47F 7/03 |
| EP | 1653234 | 5/2006 | G01N 35/02 |
| EP | 1655609 | 5/2006 | G01N 35/04 |
| JP | 60122865 U1 | 8/1985 | |
| JP | 7080355 A | 3/1995 | |
| JP | 8029432 A | 2/1996 | |
| JP | 9211005 A | 8/1997 | |
| JP | 2007/303960 | 11/2007 | G01N 35/04 |
| WO | 83/00393 | 2/1983 | |
| WO | WO 96/21855 | 7/1996 | G01N 21/01 |
| WO | WO 99/28724 | 6/1999 | G01N 1/00 |
| WO | WO 2004/004886 | 1/2004 | B01J 19/00 |
| WO | WO 2005/016526 | 2/2005 | |

OTHER PUBLICATIONS

Extended European Search Report in EP 08 01 3459, dated Jun. 24, 2009.

* cited by examiner

LABORATORY SYSTEM FOR HANDLING SAMPLE TUBE RACKS, AN ALIGNMENT ELEMENT FOR SAMPLE TUBE RACKS AND A RACK TRAY RECEIVER ASSEMBLY

TECHNICAL FIELD

The present invention relates to the handling of sample tube racks in a laboratory environment, and particularly to a laboratory device for handling sample tube racks in the context of storing such sample tubes in a storage compartment, and more particularly of placing tube racks on rack positioning areas or trays.

DESCRIPTION OF THE RELATED ART

In laboratories, such as for example clinical laboratories in which patient samples are examined and submitted to various in-vitro diagnosis tests, test tubes containing samples (such as blood, urine, etc.) have to be handled in high number and in a cautious but still efficient manner. For years now, automated procedures with corresponding systems and devices have been used in this context.

One aspect during the handling of these sample tubes relates to the tubes being placed in a storage compartment, which can be, for example, a refrigerating device. For efficient handling purposes, the tubes are not handled individually but placed in so-called storage racks. In analysers for chemical, microbiological or clinical tests, the racks are usually placed on rack carriers called trays for all further handling (transporting, charging, discharging). Usually, the trays are charged/discharged at an operating height of about 800 mm. Manual handling of the trays, especially charging/discharging of storage racks, becomes difficult when a high number of trays has to be handled.

Document JP 2007/303960 discloses a rack tray capable of setting simply a single or a plurality of racks on each desired position, and reducing a falling accident of racks, and a rack tray capable of dismounting collectively a plurality of set racks. This rack tray includes a guide part for arraying and holding a plurality of racks supporting a plurality of sample vessels and guiding the racks movably along the arraying direction. The guide part includes a plurality of engaging holding parts for holding the racks by being engaged with an engaging part of each rack when the racks are mounted.

U.S. Pat. No. 5,417,922 discloses a specimen carrier for transporting conventional specimen tubes throughout an automatic laboratory conveyance system. The carrier includes a generally rectilinear carrier body with a forward face having an identification zone delimited thereon. An identification code is marked in the identification zone so as to permit mechanical sensing and identification of the carrier on a conveyor system. A plurality of holes of various diameters and depths are provided in the top surface of the carrier to receive conventional specimen tubes of various types with the top ends of the specimen tubes located at a predetermined height above the top surface of the carrier.

SUMMARY

The present disclosure provides a laboratory system to handle sample tube racks, an alignment element for aligning the sample tube racks on a rack positioning area, a rack tray receiver assembly, and methods for handling sample tube racks.

In one aspect, a laboratory system to handle laboratory sample tube racks is provided which comprises a handling device with a gripper for gripping sample tube racks. The sample tube racks to be handled comprise a first end surface and a second end surface, the first end surface having a first surface geometry and the second end surface having a second surface geometry, and with the first and second surface geometries being different from each other. The gripper comprises a first gripping arm and a second gripping arm, with the first gripping arm having a gripping surface being complementary to the first surface geometry, and the second gripping arm having a gripping surface being complementary to the second surface geometry.

Thus, the sample tube racks with a specific geometry can be handled automatically with a gripper with two gripper arms comprising corresponding complementary geometries, respectively. This enables a secure automated handling of the racks due to the adapted geometry.

In another aspect, an alignment element for aligning sample tube racks on a primary rack positioning area of a laboratory system is provided. As above, a sample tube rack to be aligned comprises a first end surface and a second end surface, the first end surface having a first surface geometry and the second end surface having a second surface geometry. The alignment element has a bottom side, a first longitudinal side and a second longitudinal side, wherein the first longitudinal side is complementary to the first surface geometry and the second longitudinal side is complementary to the second surface geometry while the bottom side comprises a clip-like positioning element for positioning the alignment element on the rack positioning area in uniform orientation with other alignment elements on the rack positioning area.

In accordance with this aspect, automated handling of sample tube racks with a specific geometry is facilitated by ensuring correct (aligned) placement of sample tube racks on a rack positioning area.

Further features and embodiments will become apparent from the description and the accompanying drawings.

It will be understood that the features mentioned above and those described hereinafter can be used not only in the combination specified but also in other combinations or on their own, without departing from the scope of the present disclosure. The disclosure of the invention also covers the corresponding methods of operation of the disclosed devices and systems.

Various implementations are schematically illustrated in the drawings by means of an embodiment by way of example and are hereinafter explained in detail with reference to the drawings. It is understood that the description is in no way limiting on the scope of the present disclosure and is merely an illustration of a typical embodiment.

DETAILED DESCRIPTION

Reference will now be made in detail to some embodiments, examples of which are illustrated in the accompanying drawings. Wherever possible, the same reference numbers are used throughout the drawings to refer to the same or like parts.

Figure 1:
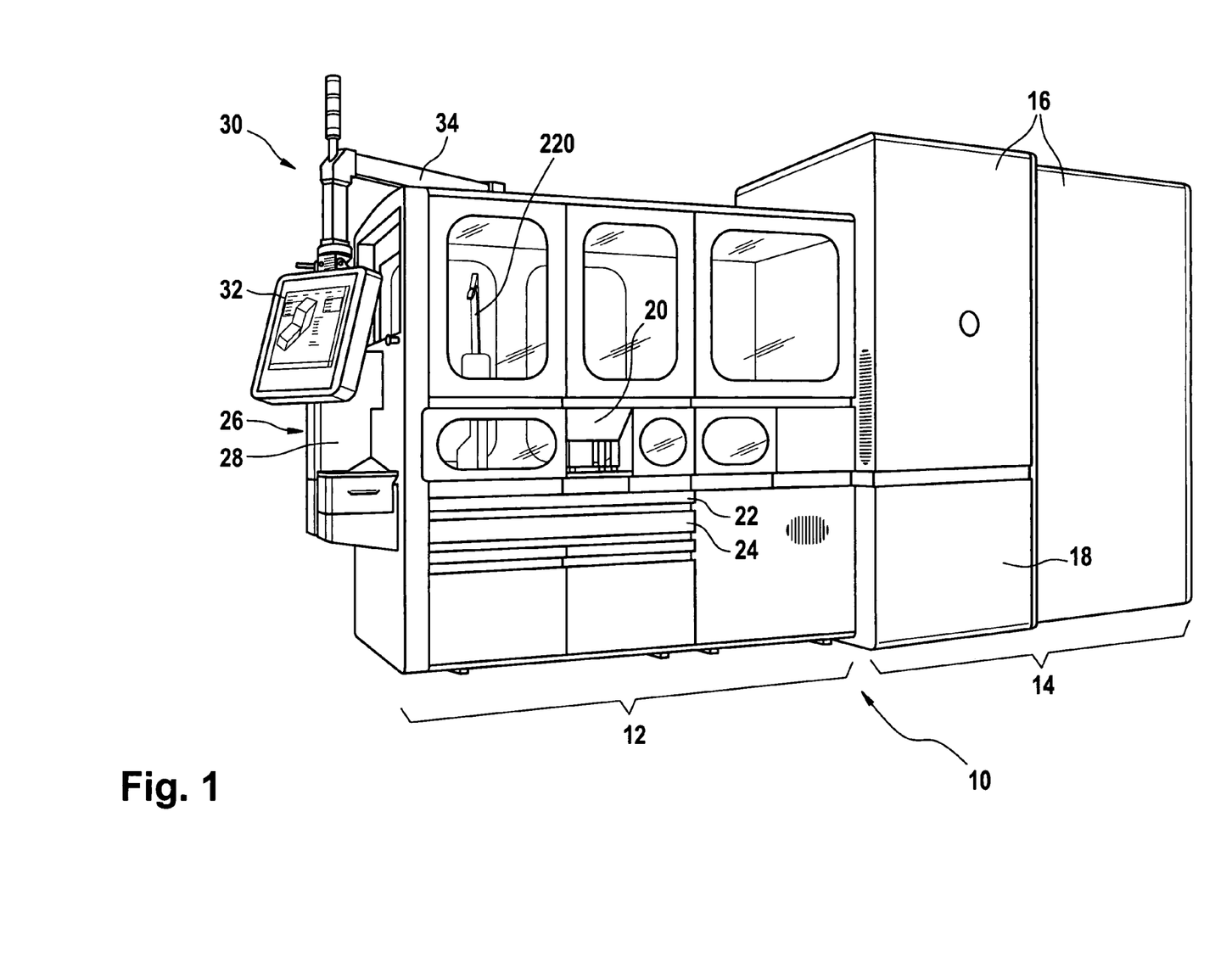
FIG. 1 shows a perspective view of a laboratory equipment unit comprising a laboratory system in which the inventive aspects of this disclosure can be implemented.

FIG. 1 shows a perspective view of a laboratory equipment unit 10 comprising a laboratory system in which the invention can be employed. This laboratory equipment unit 10 may be a so-called storage retrieval module (SRM) forming part of an overall laboratory analyser system. The storage retrieval module comprises a primary rack handler section 12 (on the left hand side of the depiction of FIG. 1) and a refrigerating or storage section 14 (on the right hand side of the depiction of FIG. 1). Between the two sections 12, 14 there is a loading/unloading interface (not shown) through which racks are transferred from the primary rack handler section 12 into the refrigerating or storage section 14 and back (in case of retrieval). This loading/unloading interface may be designed like a gate or the like.

The storage section 14 may comprise a refrigerator 16. A storage section in the context of this invention is a cabinet of various size which is able to store a plurality of sample tubes, preferably in storage racks. It may have an appropriate cooling unit to hold the ambient temperature for the tubes within the refrigerator below room temperature, possibly below 18° C. and possibly below 10° C.

In its inside, the storage section 14 comprises a plurality of shelves for storage of a high number of sample tube racks. The sample tube racks loaded into the storage section are so-called storage racks, not shown in the Figures. This implies that all tubes contained in primary racks (i.e., incoming sample tube racks of various types) fulfilling the geometry criteria of the invention are taken out of their respective primary racks and are resorted in suitable storage racks before being loaded into the storage section 14. The storage section may be large enough for one or two human beings being able to enter the inside of the storage section 14 through a door (not shown). In case the door is opened, a safety switching circuit ensures that all moving systems (like robotic arms or other transfer or conveying systems) come to a standstill, for example in a neutral or home position. While primary racks are single-row racks with somewhat standard geometry and therefore easy to handle in a plurality of different laboratory systems, the secondary racks (i.e., storage racks) are multi-row racks (e.g., three rows with more than ten positions, for example 13 to 14 positions). Therefore, the storage racks are more stable, particularly for storing purposes, and less likely to tilt over.

Further, the storage section 14 may comprise a disposal unit 18. The disposal unit 18 is connected with the storage section 14 via an internal opening (not shown) in a wall separating the storage section 14 from the disposal unit 18. Through this opening, sample tubes whose expiration date (i.e., shelf life) has elapsed can be disposed automatically through the disposal unit 18.

The primary rack handler section 12 has a housing consisting of several outer walls with windows so that operating personnel can have a direct visual overview of the rack handler's functioning. The primary rack handler section 12 comprises an opening 20 in one of the outer walls through which primary racks can be inserted into the storage retrieval module 10. The opening 20 leads to a primary rack handler area 210 (cf., FIG. 2) which comprises at least one robotic arm 220 (which can be seen in the depiction of FIG. 1 through one of the windows). The opening 20 might be closable by means of a sliding or retractable door (not shown).

The primary rack handler section 12 further comprises drawers 22, 24 through which emptied primary racks and/or primary racks containing sample tubes with error designations and/or racks containing at least one retrieved sample tube can be taken out of the storage retrieval module 10.

Further, the primary rack handler section 12 comprises a capping station 26 with a feeder tank 28 for tube caps.

The storage retrieval module 10 also comprises a man-machine interface (MMI) 30 which might have the form of a touch screen monitor 32 at the end of an articulated arm 34.

Figure 2:
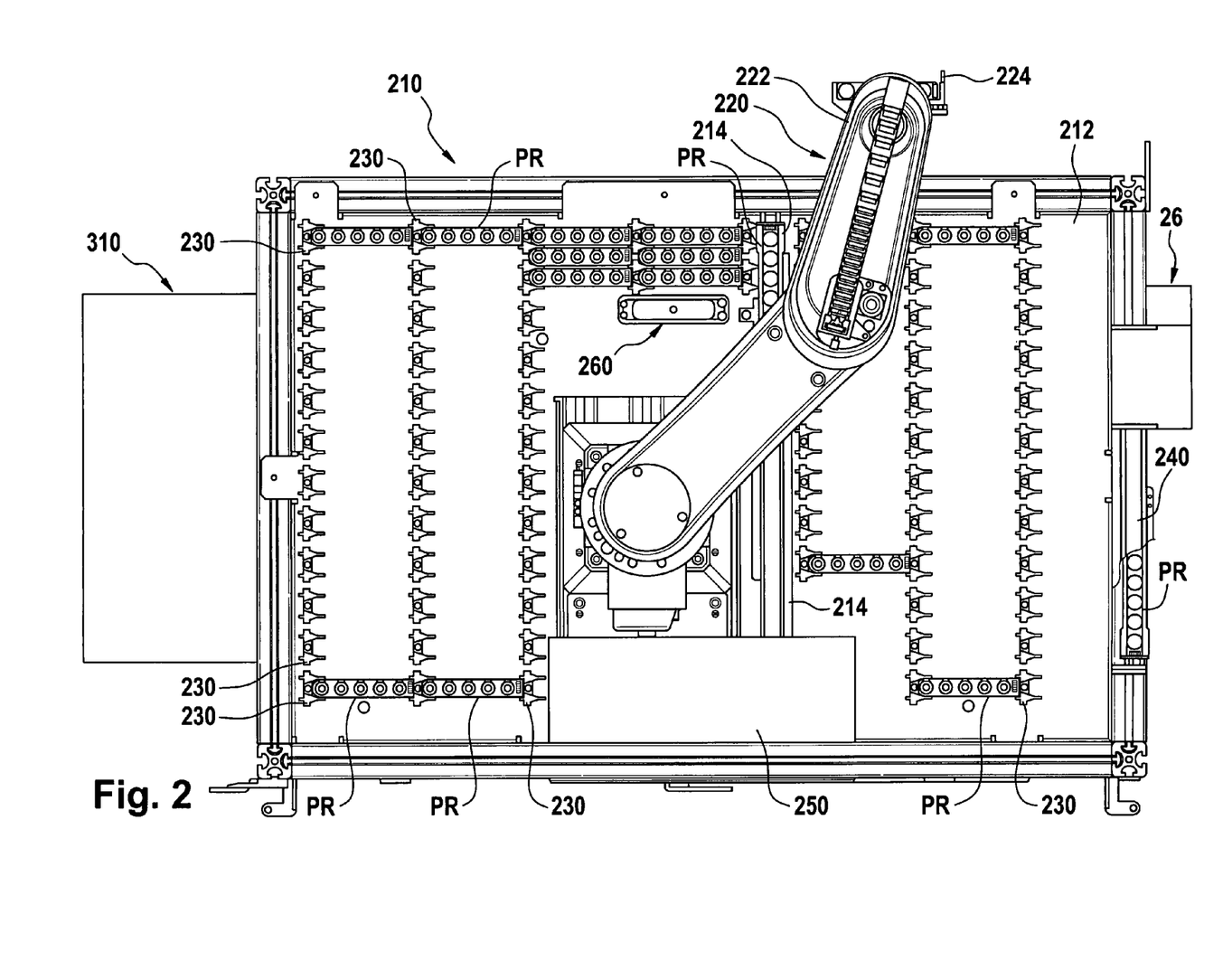
FIG. 2 shows a top view of a primary rack handler area of the laboratory system of FIG. 1 where incoming primary racks are handled.
Figure 3:
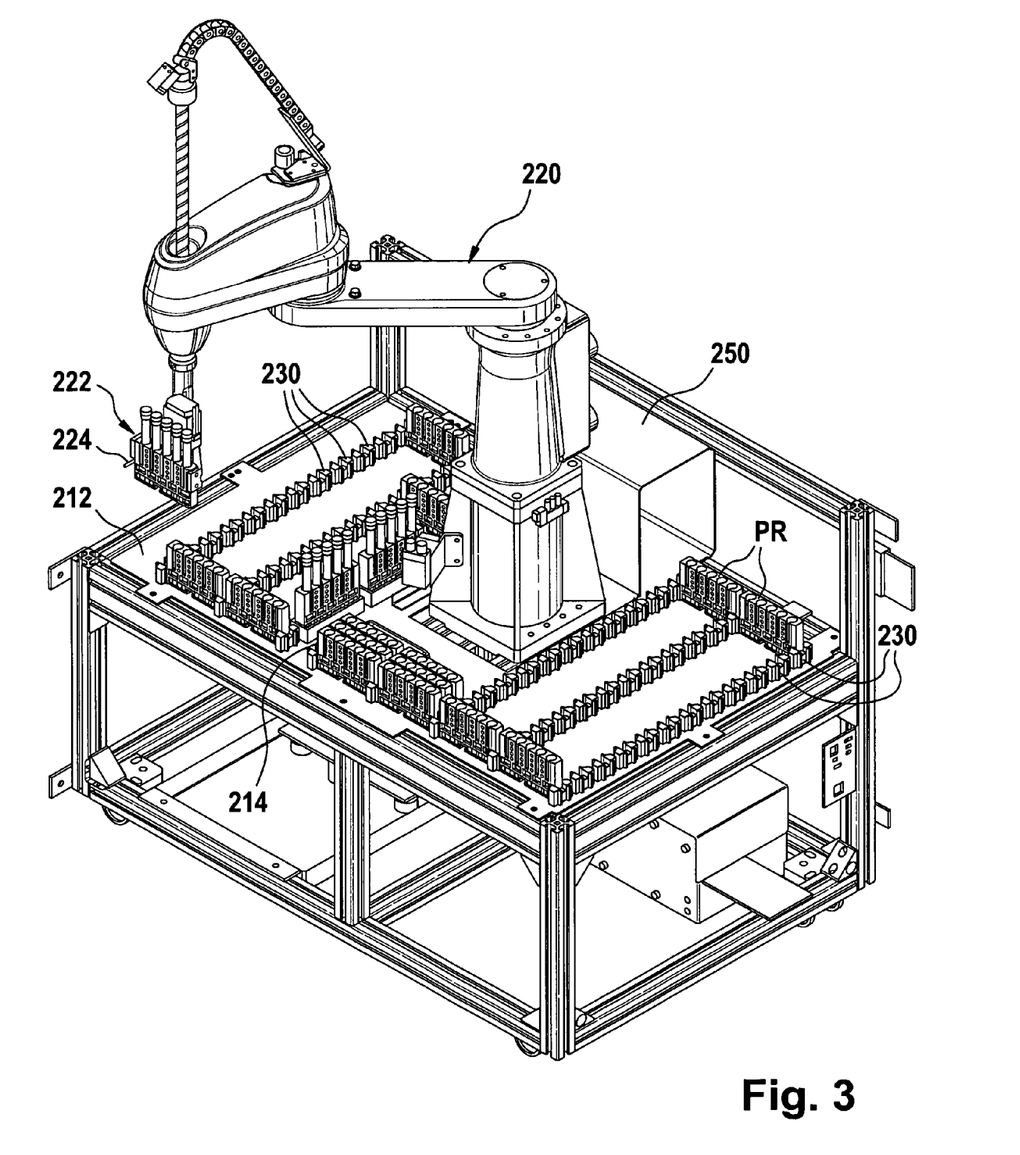
FIG. 3 shows a perspective view of the primary rack handler area of FIG. 2.

FIG. 2 shows a top view of the primary rack handler area 210 of the laboratory system of the invention and FIG. 3 shows a perspective view thereof. The primary rack handler area 210 comprises a platform 212 inside the primary rack handler section 12 of FIG. 1. It further comprises a first robotic arm 220 which may be installed essentially in the centre of the platform 212 or at least at a position from which it can reach at least all locations within the primary rack handler area 210. Any known suitable robot can be used for this purpose, such as for example a SCARA robot with four axes and four degrees of freedom. The robotic arm 220 comprises, at its end, a gripper 222 designed to securely grip the racks to be handled.

On the platform 212, a conveyor 214 is provided for conveying incoming primary racks PR containing sample tubes (e.g., five sample tubes) to an image analysing unit 250 which is also positioned on the platform 212.

Further, a plurality of alignment elements 230 are provided on the platform 212. The alignment elements 230 are designed to hold in place the primary racks PR in a desired alignment or orientation which corresponds to an orientation of the gripper 222 of the robotic arm 220. In order to ensure proper orientation of the primary racks PR in every step of processing (such that the sample tubes positions are always unambiguously identifiable), the primary racks may not be introduced directly on the conveyor 214 through the opening 20 but rather be taken up by the gripper 222 of robotic arm 220 and then placed on the conveyor 214. For this, a receiving position (not shown) for incoming racks is provided from which the robotic arm then takes up the incoming rack in order to place it onto the conveyor 214.

The conveyor 214 conveys the primary rack into the image analysing unit 250 where the sample tubes in the primary rack are analysed as to their geometry parameters. The determined geometry parameters of each sample tube are compared with predetermined geometry criteria and it is identified whether a sample tube is system conform or not. One of the geometry parameters to be analysed is the presence of a cap on the sample tube, and another geometry parameter to be analysed is the tube's diameter.

In case a sample tube is found to have no cap, the whole primary rack is sent to the capping station 26 (not shown in FIG. 3) before any other further processing of the primary rack or any of the other sample tubes contained therein. For this, the first robotic arm 220 places the primary rack onto the conveyor 260 conveying the primary rack with its sample tubes into the capping station 26 for a re-capping of the sample tube(s) identified to have no cap. After successful re-capping of the sample tube(s), the primary rack is brought back into the regular processing. Alternatively, as the case may be, the primary rack can be transferred back into the image analysing unit 250 in order to make sure that now all sample tubes carry a cap and are fit for further processing.

Figures 4, 5:
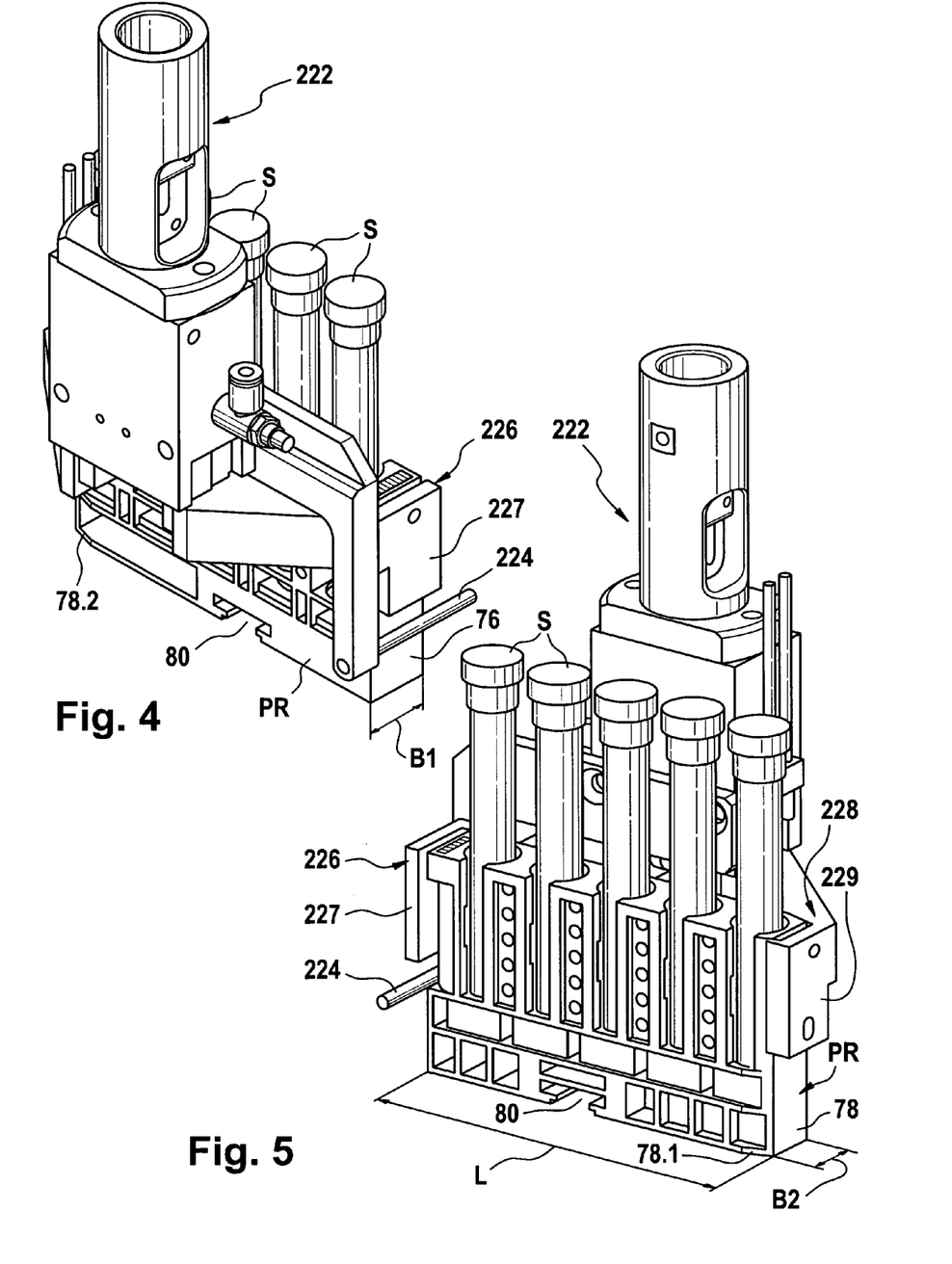
FIG. 4 shows a rear perspective view of a gripper of a robotic arm of the primary rack handler area of FIG. 2.
FIG. 5 shows a front perspective view of the gripper of FIG. 4.

FIGS. 4 and 5 show an enlarged view of the gripper 222 of the robotic arm 220. The gripper 222 comprises a first arm 226 and a second arm 228. The two arms 226, 228 function according to the principle of tongs, i.e. they can perform a relative movement towards each other in order to grip a primary rack between them. The distance between the two arms 226, 228 is such that they can grip a primary rack in its longitudinal extension, or with other words, the distance between the two arms in their gripping positioning is slightly larger than the length L of a primary rack PR.

Each primary rack PR comprises a first end surface 76 and a second end surface 78, the first end surface 76 having a first surface geometry and the second end surface 78 having a second surface geometry. In the embodiment of the drawings, the first end surface 76 is a flat surface whereas the second surface 78 geometry has two bevelled edges 78.1 and 78.2. Accordingly and as already described above, the primary racks PR have an orientation due to the geometry of their end surfaces which allows unambiguous identification of the sample tubes positions.

In order to be able to properly and safely grip the primary racks, each of the two arms 226, 228 of the gripper 222 has complementary surfaces relative to the surface geometry of the end surfaces of the primary racks. Namely, the first gripper arm 226 has a gripping surface being complementary to the first surface geometry (flat surface 76) and the second gripping arm 228 has a gripping surface being complementary to the second surface geometry (bevelled edges 78.1, 78.2).

Further, the two arms 226, 228 are formed as horizontal tongs so as to encompass and grip the primary rack in a horizontal plane. This avoids rack handling from above and thus the danger of breaking sample tubes being too high or not being fully inserted in the rack opening. It also allows moving primary racks horizontally and inserting them into trays in shelves (cf. FIG. 12).

Figure 6:
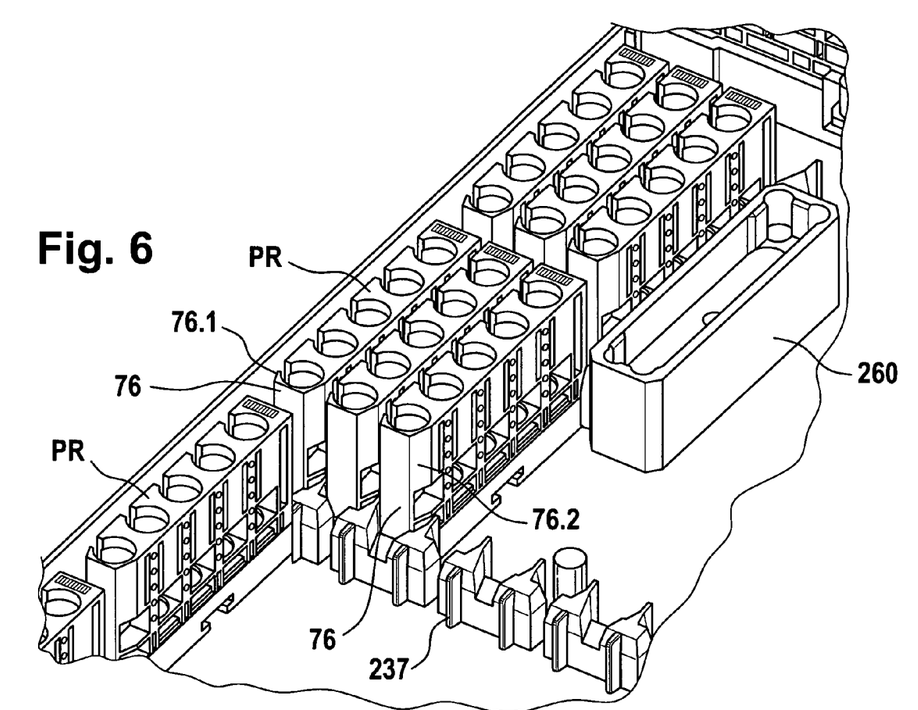
FIG. 6 shows a detail perspective view of the primary rack handler area of FIGS. 2 and 3.
Figure 7:
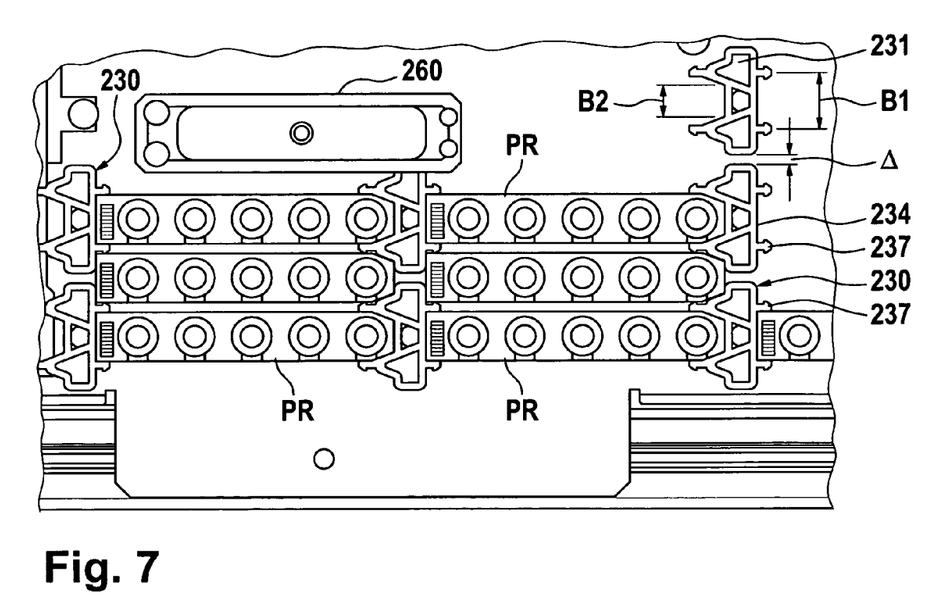
FIG. 7 shows a top view of the detail of FIG. 6.

In order to be able to grip primary racks from above when several racks are placed next to each other as illustrated in FIGS. 6 and 7, the two arms 226, 228 of the gripper 222 each comprise a downwardly extending extension 227, 229 which allows a gripping of the top portion of each end surface 76, 78 of the primary rack PR in order to lift the same up. The primary rack PR is then placed in an intermediate or interim parking position 260, the gripper 222 releases the primary rack PR in the parking position 260, the robotic arm 220 lowers the gripper 222 slightly and then the two arms close and fully grip the primary rack with their full gripping surface (cf. FIG. 5). This way, the primary racks PR can be stocked, e.g. on the platform 212 as rack positioning area, next to each other without losing space even though the gripping is done "from behind".

Figures 8, 9, 10:
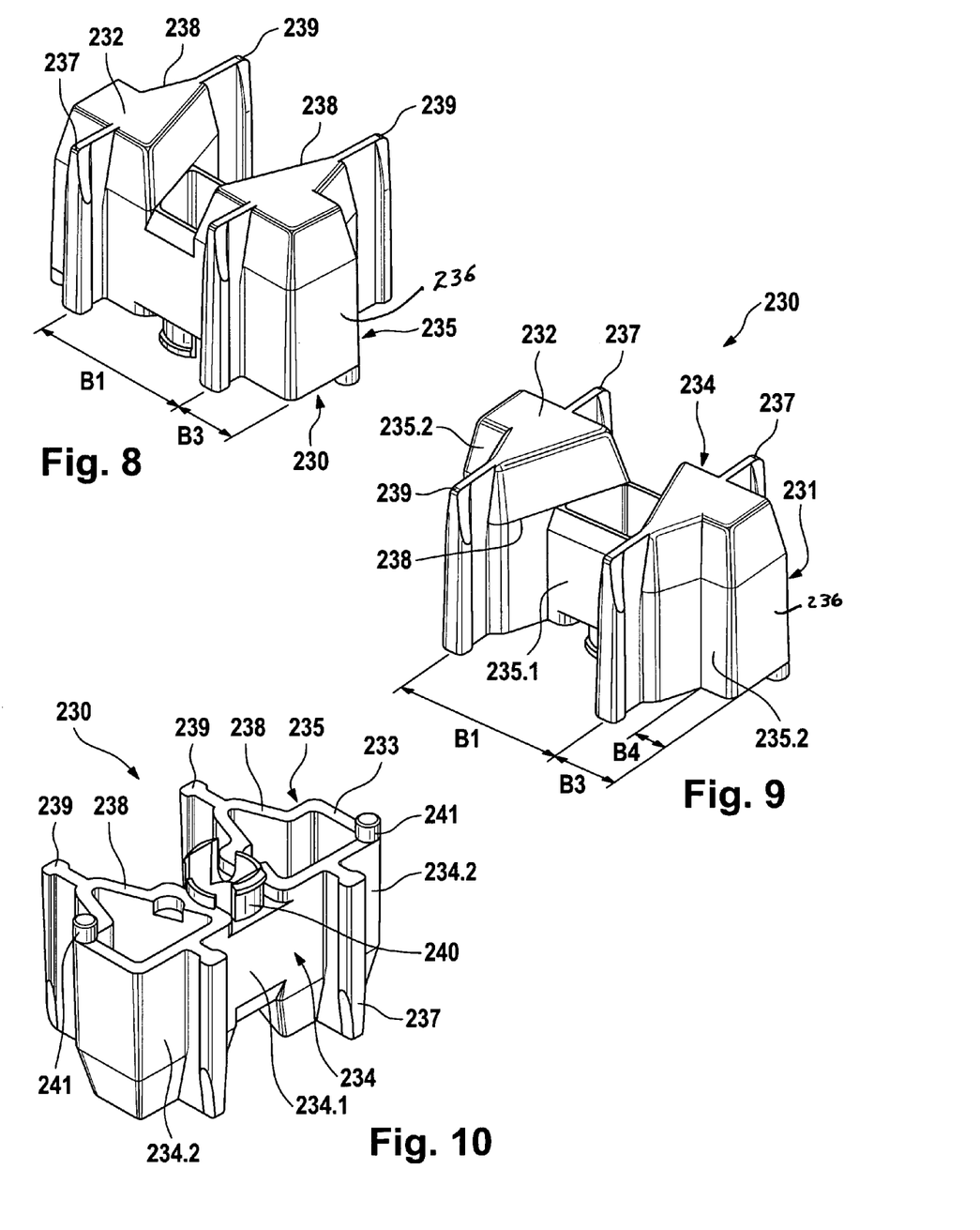
FIG. 8 shows a first perspective top view of an alignment element a multitude of which are used to align the primary racks in the primary rack positioning area as shown in FIG. 2.
FIG. 9 shows a second perspective top view of the alignment element of FIG. 8.
FIG. 10 shows a perspective bottom view of the alignment element of FIG. 8.

FIGS. 8 to 10 show enlarged depictions of the alignment element 230, a multitude of which are used to align the primary racks (PR) on the rack positioning area or platform 212 as shown in FIG. 2. The alignment element 230 comprises a base body 231 with a top surface 232, a bottom surface 233, a first longitudinal side 234, a second longitudinal side 235, and first and second end sides 236.

The first longitudinal side 234 of the alignment element 230 has a substantially flat surface and is provided with two vertical partition extensions 237, dividing the first longitudinal side 234 into a main centre section 234.1 and two smaller adjacent outer sections 234.2. The breadth B1 of the main centre section 234.1 equals substantially the breadth of the flat first end surface 76 of the primary rack PR so that this end surface of the primary rack can be received in between the two vertical partition extensions 237. The breadth B3 of the two smaller outer sections 234.2 each equals (B1−Δ)/2 wherein Δ is the width of the gap between two adjacent alignment elements 230 when positioned on the rack positioning area, i.e. the platform 212. As a result of this geometry, an end surface 76 of the primary rack PR can also be received in between two vertical partition extensions 237 of adjacent alignment elements 230 which allows an optimised use of the available space for stocking or interim parking the primary racks.

The second longitudinal side 235 of the alignment element 230 (shown in FIG. 10) comprises, symmetrically to the two vertical partition extensions 237 of the opposite first longitudinal side 234, two projections 238 with substantially triangular cross-section, creating a second main centre section 235.1 and two smaller second outer sections 235.2 (see FIG. 9). At the peak of each of the projections 238, respectively, a vertical extension 239 is provided, similar to the two vertical partition extensions 237 of the opposite first longitudinal side 234 and exactly opposing these. Therefore, the distance between the two vertical extensions 239 equals the breadth B1 of the opposing first main centre section 234.1, whereas the breadth B2 of the second main centre section 235.1 between the two projections 238 equals substantially the breadth of the second end surface 78 of the primary rack PR with two bevelled edges so that this bevelled end surface of the primary rack can be received in between the two projections 238 (see FIG. 7). Again, the breadth B4 of the two second outer sections 235.2 each equals half of the breadth B2 minus half of the gap between two alignment elements, i.e. B4=(B2−Δ)/2.

The top surface 232 of the alignment element 230 may comprise bevelled edges in order to facilitate insertion of a primary rack between the extensions 237, 239 and projections 238.

On its bottom side 233, the alignment element 230 has a clip-like positioning element 240 provided in the centre of the bottom side 233. It further comprises two positioning pins 241 diagonally opposing each other (see FIG. 10).

FIGS. 11 to 14 show a primary rack tray receiver assembly 710 which receives a tray 720 containing one or more primary racks PR for loading onto the platform 212 of FIG. 2 and subsequent sorting of sample tubes contained therein.

Figure 11:
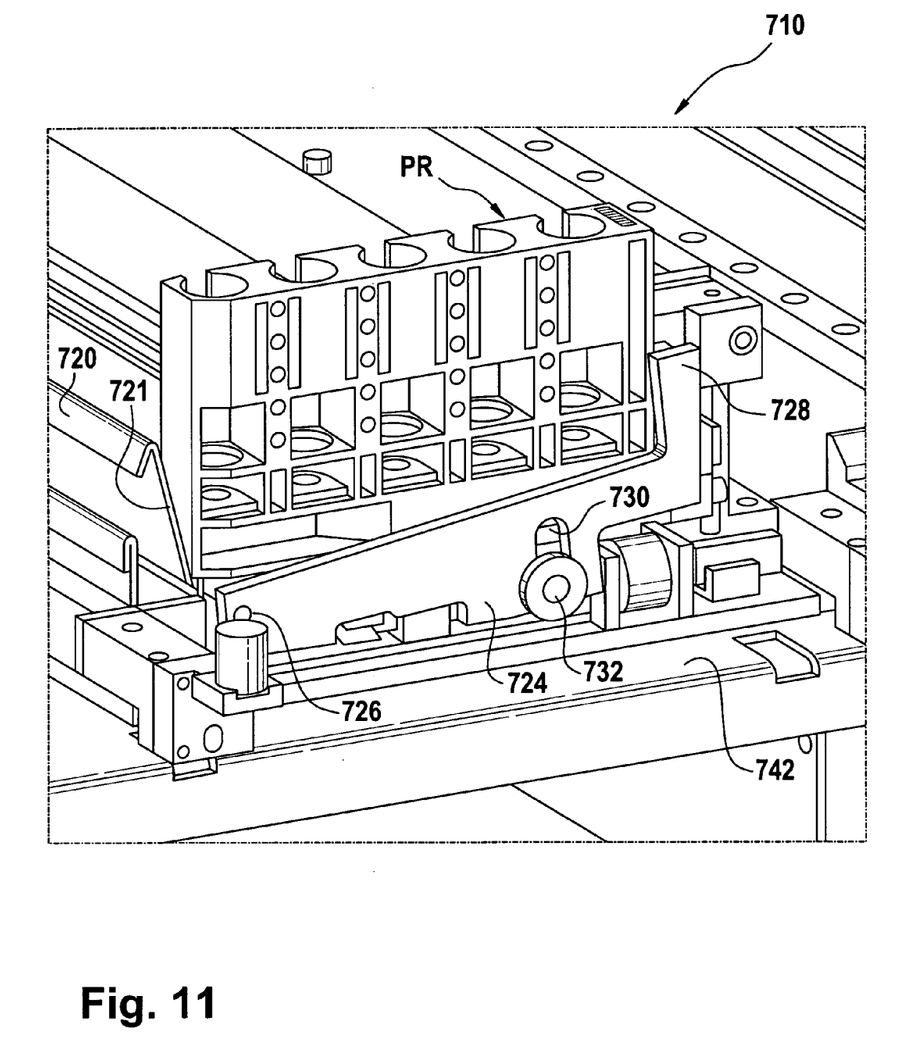
FIG. 11 shows a perspective view of a primary rack tray receiver assembly with barrier mechanism.

The primary rack tray receiver assembly 710 comprises a receiver skid 712 which is moveable along a skid rail 714. The skid rail 714 extends along a longitudinal extension of the primary rack tray receiver assembly 710, the longitudinal extension having a length adapted to accommodate a primary rack tray 720.

The receiver skid 712 is designed to receive a primary rack tray 720 for locking engagement therewith. To this end, and with reference to FIG. 14, the receiver skid 712 comprises receiving and fastening means 716, 718, 722, namely two openings 716 and 718 in its substantially flat top surface which are adapted to engage with corresponding protrusions (not shown) of the primary rack tray 720. In at least one of the openings 716, a retractable bolt 722 is provided which is designed to snap into a corresponding recess of the protrusion of the primary rack tray 720 when inserted in the receiver skid 712. The snapping direction of the retractable bolt 722 may be, for example, perpendicular to the direction of insertion of the primary rack tray 720.

Figure 12:
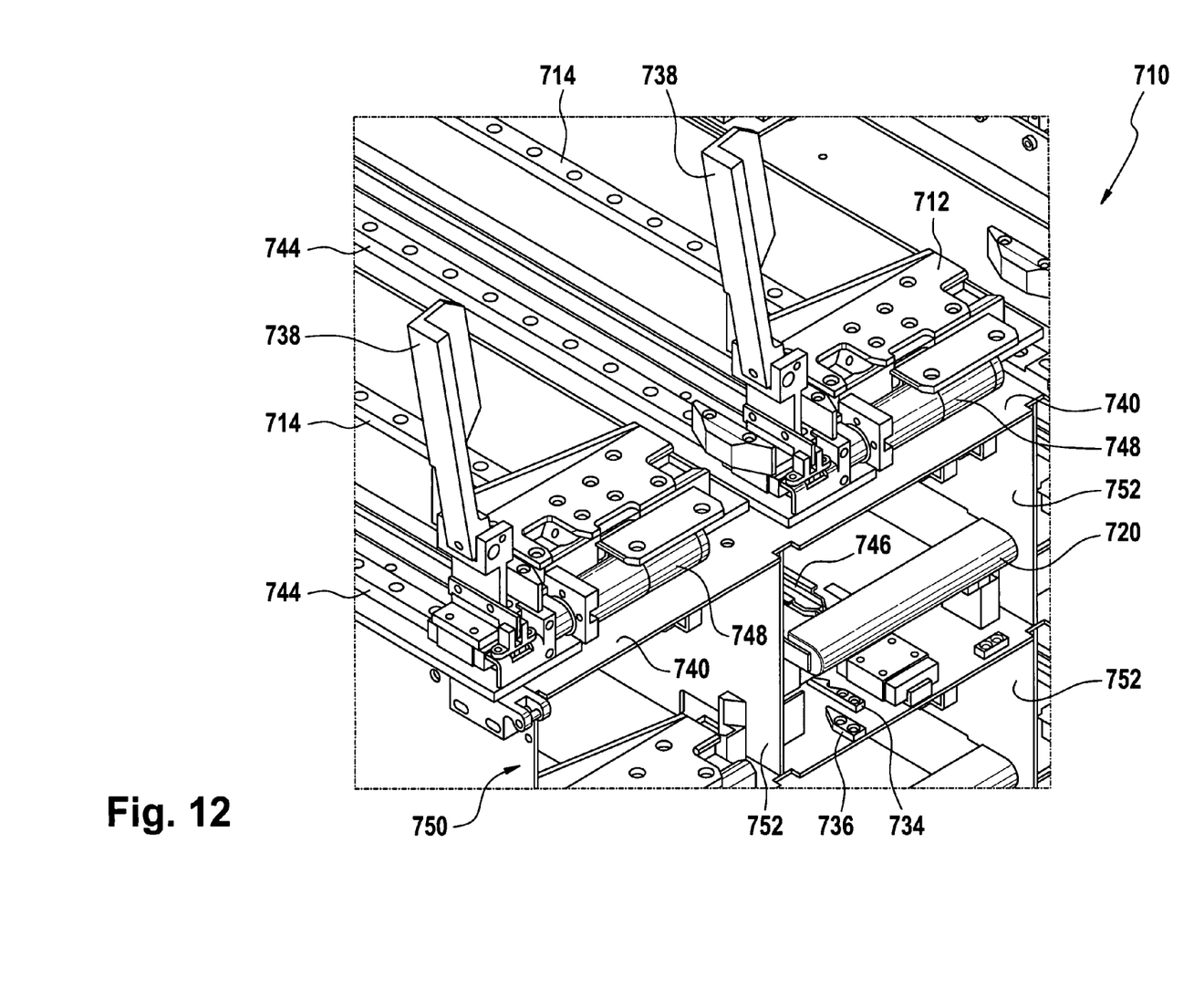
FIG. 12 shows another perspective view of a primary rack tray receiver assembly of FIG. 11.

The empty receiver skid 712 is located at one end 740 (first end) of the longitudinal extension of the primary rack tray receiver assembly (cf. FIG. 12). This position might be called the waiting position. Once a primary rack tray 720 is inserted in the receiver skid 712 and fastened thereto, the receiver skid 712 is pushed, together with the inserted primary rack tray 720, along the skid rails 714 out of its waiting position towards an opposing end 742 of the longitudinal extension of the primary rack tray receiver assembly.

When the primary rack tray 720 is inserted into the primary rack tray receiver assembly 710, a pivotally arranged barrier gate 738 may be swung downwards. The barrier gate 738 is slidably coupled to a barrier rail 744 and can be moved longitudinally along the barrier rail 744. The movement may be guided by an electric motor 748 with the effect to apply a controlled push force against a stack of primary racks loaded on the primary rack tray 720. This movement occurs for example after a primary rack has been unloaded from the primary rack tray 720 at the opposing end 742 of the primary rack tray receiver assembly in order to recompose the stack and to ensure that the next primary rack is in an unloading position.

In order to improve stability and movement of the primary rack from one end of the primary rack tray 720 to the other, the primary rack tray 720 may comprise a rack trail 746 extending longitudinally along the length of the primary rack tray 720, wherein the rack trail 746 is so designed to slidably engage with a recess 80 located on the bottom side of a primary rack (see, FIGS. 4, 5 & 12).

The receiver skid 712 may further comprise a barrier element 724 which is pivotally linked to a longitudinal side of the receiver skid 712 with a first end 726 and being biased into an upwardly inclined position across the open front end 721 of the primary rack tray 720, thus preventing racks PR in the primary rack tray 720 from falling out through the open front end 721 during the insertion and moving procedure as well as during the subsequent handling procedure. The barrier element 724 may comprise a guide slot 730 with a guide pin 732 of the receiver skid 712 extending therethrough (see FIGS. 11 & 13).

Figure 13:
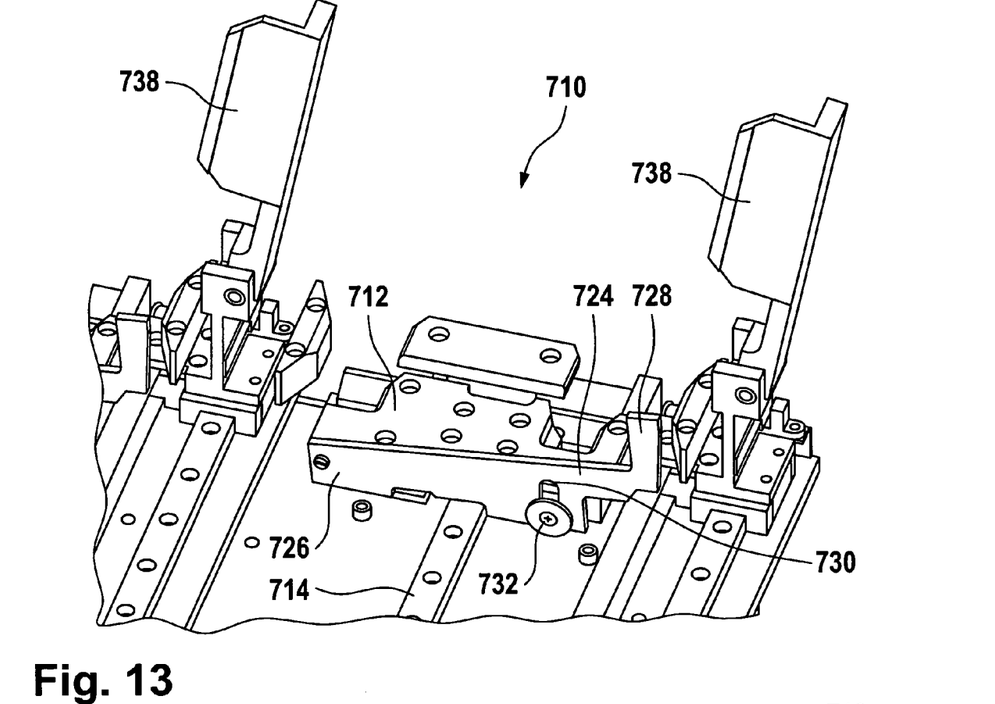
FIG. 13 shows a further perspective view of the primary rack tray receiver assembly of FIGS. 11 and 12.
Figure 14:
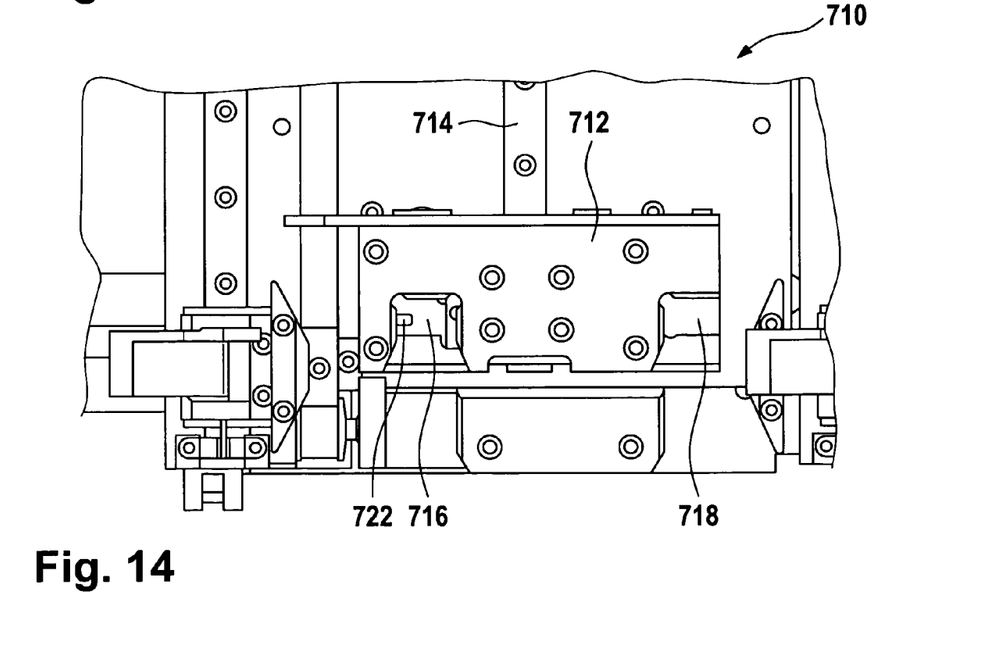
FIG. 14 shows a plan top view of the primary rack tray receiver assembly of FIG. 12.

The barrier element 724 can be pushed down against its biasing force around the pivotal axis at the first end 726 and along guide slot 730. When pushed down against the biasing force, the open front end 721 of the primary rack tray 720 is set free and the first placed rack PR can be taken out easily. When the barrier element 724 is released, i.e. the pushing down force is taken off, it snaps up again due to the biasing force, thus closing again the open front end 721 of the primary rack tray 720.

In order to facilitate the pushing down of the barrier element 724, the barrier element 724 may comprise at an opposing second end a vertical elongation 728 with the function of an actuating lever. Automated pushing down of the barrier element 724 by means of the robotic arm 220 can be achieved by means of a corresponding bolt 224 extending from the gripper 222 of the robotic arm 220 (see FIG. 3). The bolt 224 is attached to the gripper 222 in such a manner that it extends substantially horizontally below the gripper 222 and beyond the outer circumference of a primary rack PR when gripped by the gripper 222 at a front end 76 of the rack PR, i.e. the bolt 224 extends perpendicular to the longitudinal axis of the primary rack PR (cf. FIGS. 4 and 5).

When the robotic arm 220 intends to pick up the first place primary rack (PR) in the primary rack tray 720, it lowers the gripper 222 down towards the primary rack (PR), with the result that the bolt 224 contacts the upper end of the lever 728. The downward movement of the gripper 222 continues, thus pushing down the barrier element 724 due to the force exerted on the lever 728. Then, the gripper arms 226, 228 grip the primary rack (PR), and the primary rack (PR) is then taken out of the primary rack tray 720 with a horizontal movement (which is possible as the barrier element 724 is pushed down). Because the bolt 224 extends beyond the outer circumference of the primary rack (PR), the bolt 224 stays in contact with the lever 728 long enough for the primary rack (PR to be fully taken out of the primary rack tray 720, so that the barrier element 724 only snaps up again when the primary rack tray is removed.

If a primary rack tray 720 is to be removed from the primary rack tray receiver assembly, the gate barrier 738 is lifted up and the primary rack tray 720 is pulled out of the primary rack tray receiver assembly 710, thereby moving the receiver skid 712 back along the skid rail 714. When the receiver skid is brought back into its waiting position, the retractable bolt 722 is retracted out of the recess of the primary rack tray 720 against a biasing force. In particular, when the receiver skid 712 reaches its waiting position at 740, the biasing mechanism of the retractable bolt 722 hits a ramp-like element 736 on the bottom of the primary rack tray receiver assembly 710 which causes the bolt 722 to be retracted against its biasing force and thus to unlock the primary rack tray 720 in the receiver skid 712 so that the primary rack tray 720 can be removed. Additionally, a latching element 734 can be provided in order to lock the receiver skid 712 in its movement. Typically, the latching element 734 is arranged somewhat before the ramp-like element 736 so as to allow locking of the movement of the receiver skid 712 without necessarily having to retract the bolt 722. Only if the receiver skid 712 is pulled further back against the ramp-like element 736, the bolt 722 will be retracted and the primary rack tray 720 released. See FIG. 12.

FIG. 12 further illustrates a rack shelf system 750 comprising a plurality of shelf compartments 752, each of the shelf compartments comprising a primary rack tray receiver assembly and as illustrated in FIG. 11 and described above. The rack shelf system 750 allows handling of laboratory sample tube racks in a high number even if only little space is available. The rack shelf system 750 works particularly well in combination with the robotic gripper 222 as described and disclosed herein which allows a horizontal gripping of the primary racks PR as this opens the possibility to also insert, i.e. load primary racks PR into rack place in a shelf with a horizontal movement (which is not possible with a gripper gripping racks from above). This loading procedure works analogously to the above-described unloading procedure of racks from a primary rack tray.

According to other typical embodiments, upper or top shelf tray receiver assemblies receive rack trays loaded with primary racks to be unloaded (by the robotic arm 220), while lower shelf compartments receive empty rack trays to be loaded with primary racks.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A laboratory system to handle laboratory sample tube racks, comprising a robotic arm (220) with a gripper (222) for gripping sample tube racks, and a rack tray receiver assembly (710), wherein the gripper (222) comprises a locking/unlocking bolt (224) extending from the gripper, and wherein the rack tray receiver assembly (710) comprises:
 a rack tray (720) having an open front end (721) carrying one or more sample tube racks;
 a skid rail (714);
 a receiver skid (712) movable along the skid rail (714), the receiver skid (712) comprising receiving and fastening means (716, 718, 722) for fastening the rack tray (720) on the receiver skid (712), the rack tray (720) being inserted into the receiving and fastening means (716, 718, 722), the receiver skid further comprising a barrier element (724);
 wherein the open front end (721) abuts the barrier element (724), the barrier element (724) being pivotally linked to the receiver skid (712) and being biased into a position across the open front end (721) of the rack tray (720), thereby preventing sample tube racks in the rack tray (720) from falling out through the open front end (721).

2. The laboratory system of claim 1, wherein the sample tube racks to be handled comprise a first end surface (76) and a second end surface (78), the first end surface (76) having a first surface geometry and the second end surface (78) having a second surface geometry, and wherein the gripper (222) comprises a first gripping arm (226) and a second gripping arm (228), with the first gripping arm (226) having a gripping surface being complementary to the first surface geometry, and the second gripping arm (228) having a gripping surface being complementary to the second surface geometry.

3. The laboratory system of claim 2, wherein the first and second gripping arms (226, 228) are formed as horizontal tongs so as to encompass and grip the sample tube rack in a horizontal plane.

4. The laboratory system of claim 2, wherein the gripping arms (226, 228) each comprise a downwardly extending extension (227, 229), respectively, which allows a gripping of a top portion of each end surface (76, 78) of the sample tube rack.

5. The laboratory system of claim 1, wherein the rack tray receiver assembly further comprises a longitudinal extension, having a first end (740) and an opposite end (742), the extension having a length adapted to accommodate a rack tray (720), wherein the receiver skid (712) is located at the first end (740) of the longitudinal extension in its waiting position and is pushed along the skid rail (714) to the opposite end (742) of the longitudinal extension when the rack tray (720) is inserted.

6. The laboratory system of claim 1, wherein the rack tray receiver assembly further comprises a longitudinal extension with a length adapted to accommodate a rack tray (720) and having a first end (740) and an opposite end (742), and wherein
 the receiving and fastening means (716, 718, 722) comprise a retractable bolt (722) which snaps into a corresponding recess of the rack tray (720) when the rack tray (720) is inserted in the receiver skid (712) and the receiver skid (712) is being moved out of its waiting position.

7. The laboratory system of claim 1, further comprising a rack shelf (750) with a plurality of shelf compartments (752), wherein each shelf compartment (752) comprises a rack tray receiver assembly (710).

8. The laboratory system of claim 2, wherein the first surface (76) geometry is a flat surface, and the second surface (78) geometry has two bevelled edges (78.1 and 78.2).

9. A method for handling laboratory sample tube racks with a robotic arm (220) comprising a gripper (222) for gripping the sample tube racks, wherein the gripper (222) comprises a first gripping arm (226) and a second gripping arm (228) which are formed as horizontal tongs, wherein several sample tube racks are placed in parallel next to each other, the method comprising the sequential steps of:
 (a) the robotic arm (220) gripping a first area of a sample tube rack to be picked up vertically from above by means of extensions (227, 229) extending downwardly from the first and second gripping arms (226, 228),
 (b) placing the sample tube rack in an intermediate parking position (260),
 (c) lowering the gripper (222) relative to the first area of the sample tube rack, and
 (d) closing the first and second gripping arms (226, 228) about a second area of the sample tube rack, thereby fully gripping the sample tube rack with the first and second gripping arms.

10. The method of claim 9, wherein in step (d) the gripping arms encompass and grip the sample tube rack in a horizontal plane.

* * * * *